(12) United States Patent
Chang

(10) Patent No.: US 10,066,816 B2
(45) Date of Patent: Sep. 4, 2018

(54) MEDICAL/DENTAL HEADLAMP WITH ADJUSTABLE PROXIMITY ON/OFF SENSOR

(71) Applicant: General Scientific Corporation, Ann Arbor, MI (US)

(72) Inventor: Byung J. Chang, Ann Arbor, MI (US)

(73) Assignee: General Scientific Corp., Ann Arbor, MI (US)

( * ) Notice: Subject to any disclaimer, the term of this patent is extended or adjusted under 35 U.S.C. 154(b) by 0 days.

(21) Appl. No.: 15/136,380

(22) Filed: Apr. 22, 2016

(65) Prior Publication Data

US 2016/0238220 A1 Aug. 18, 2016

Related U.S. Application Data

(63) Continuation-in-part of application No. 14/302,899, filed on Jun. 12, 2014, now abandoned, which is a
(Continued)

(51) Int. Cl.
| | |
|---|---|
| *F21V 21/084* | (2006.01) |
| *F21V 23/04* | (2006.01) |
| *A61B 90/35* | (2016.01) |
| *H05B 33/08* | (2006.01) |
| *H05B 37/02* | (2006.01) |
| *A61B 90/30* | (2016.01) |

(Continued)

(52) U.S. Cl.
CPC ............ *F21V 21/084* (2013.01); *A61B 90/30* (2016.02); *A61B 90/35* (2016.02); *F21V 23/0471* (2013.01); *H05B 33/0854* (2013.01); *H05B 37/0227* (2013.01); *A61B 2090/309* (2016.02); *A61B 2090/502* (2016.02); *F21L 4/06* (2013.01); *F21W 2131/20* (2013.01); *F21Y 2115/10* (2016.08); *Y02B 20/44* (2013.01)

(58) Field of Classification Search
CPC .............. F21V 21/084; F21V 23/0471; A61B 2090/502; A61B 90/30; F21W 2131/20; H05B 33/0854

See application file for complete search history.

(56) References Cited

U.S. PATENT DOCUMENTS

| | | | |
|---|---|---|---|
| 2006/0044800 A1* | 3/2006 | Reime | ............... H05B 33/0803 362/276 |
| 2008/0310145 A1* | 12/2008 | Blake | .................... A61B 90/35 362/105 |

(Continued)

*Primary Examiner* — Evan Dzierzynski
(74) *Attorney, Agent, or Firm* — John G. Posa; Belzer PC

(57) ABSTRACT

A headlight incorporates an infrared sensor enabling the light to be turned ON and OFF without physical contact. The system includes a light source and a mechanism for coupling the light source to eyeglass frames or to a headband. A power supply and control unit is disposed remotely from the light source and is interconnected to the light source through an electrical cable. An infrared (IR) motion sensor is interconnected to the power supply and control unit, and electrical circuitry within the power supply and control unit is operative to turn the light source ON and OFF is response to the detection of a hand or other body part by the sensor. In the preferred embodiment, the light source includes a light-emitting diode (LED), and the IR detector is user-adjustable to set the ON/OFF activation distance in accordance with user preferences.

13 Claims, 5 Drawing Sheets

Related U.S. Application Data continuation-in-part of application No. 13/929,394, filed on Jun. 27, 2013, now abandoned.

(51) Int. Cl.
*F21W 131/20* (2006.01)
*F21L 4/06* (2006.01)
*A61B 90/50* (2016.01)
*F21Y 115/10* (2016.01)

(56) References Cited

U.S. PATENT DOCUMENTS

| | | | | |
|---|---|---|---|---|
| 2010/0289735 | A1* | 11/2010 | Hosogi | G09G 3/3406 345/102 |
| 2011/0245637 | A1* | 10/2011 | McKenna | A61B 5/14552 600/310 |
| 2012/0139877 | A1* | 6/2012 | Kawabe | G06F 1/1643 345/175 |
| 2012/0206050 | A1* | 8/2012 | Spero | B60Q 1/04 315/152 |
| 2012/0275140 | A1* | 11/2012 | Feinbloom | F21L 14/00 362/105 |
| 2013/0111600 | A1* | 5/2013 | Guenther | G06F 21/72 726/26 |

\* cited by examiner

US 10,066,816 B2

MEDICAL/DENTAL HEADLAMP WITH ADJUSTABLE PROXIMITY ON/OFF SENSOR

REFERENCE TO RELATED APPLICATIONS

This application is a continuation-in-part of U.S. patent application Ser. No. 14/302,899, filed Jun. 12, 2014, which is a continuation-in-part of U.S. patent application Ser. No. 13/929,394, filed Jun. 27, 2013, the entire content of both applications being incorporated herein by reference.

FIELD OF THE INVENTION

This invention relates generally to headlights of the type used by surgeons, medical and dental practitioners and, in particular, to a motion-activated headlamp.

BACKGROUND OF THE INVENTION

It is common for surgeons and medical/dental practitioners to wear headlights to enhance vision. Typical headlights using light-emitting diodes and optical fibers may be found at http://surgitel.com/headlights.

With such systems, the headlight contains only the light source and beam-forming optics. The power supply is disposed remotely, and may be belt-worn, for example.

One of the problems with existing systems is that the control unit may not be sterilized, such that the practitioner's hand may become contaminated if the light is turned ON or OFF during a procedure.

SUMMARY OF THE INVENTION

This invention is directed to a headlight with an infrared sensor enabling the light to be turned ON and OFF without physical contact. The system includes a light source and a mechanism for coupling the light source to eyeglass frames or to a headband. A power supply and control unit is disposed remotely from the light source and is interconnected to the light source through an electrical cable. An infrared (IR) motion sensor is interconnected to the power supply and control unit, and electrical circuitry within the power supply and control unit is operative to turn the light source ON and OFF is response to the detection of a hand or other body part by the sensor.

In the preferred embodiment, the light source includes a light-emitting diode (LED), and the IR detector is a passive or an active IR sensor. A mechanism may be provided to attach the IR sensor to clothing, the IR sensor to the eyeglass frames, the headband, or the light source. The light source and IR sensor may be interconnected to an electrical coupler through separate cables, with a combination cable being used to interconnect the light source and IR sensor to the power supply and control unit through a single combination cable. The preferred embodiment includes an adjustable-proximity ON/OFF control enabling the activation distance to be customized for different user preferences.

DETAILED DESCRIPTION OF THE INVENTION

This invention is directed to a headlight with an infrared sensor enabling the light to be turned ON and OFF without physical contact. As such, the invention is ideally suited for surgical, medical and dental applications wherein a sterile field may be compromised through manual contact. While in the preferred embodiments the light source comprises one or more light-emitting diodes (LEDs), the invention is not limited in terms of the light source used.

Figure 1:
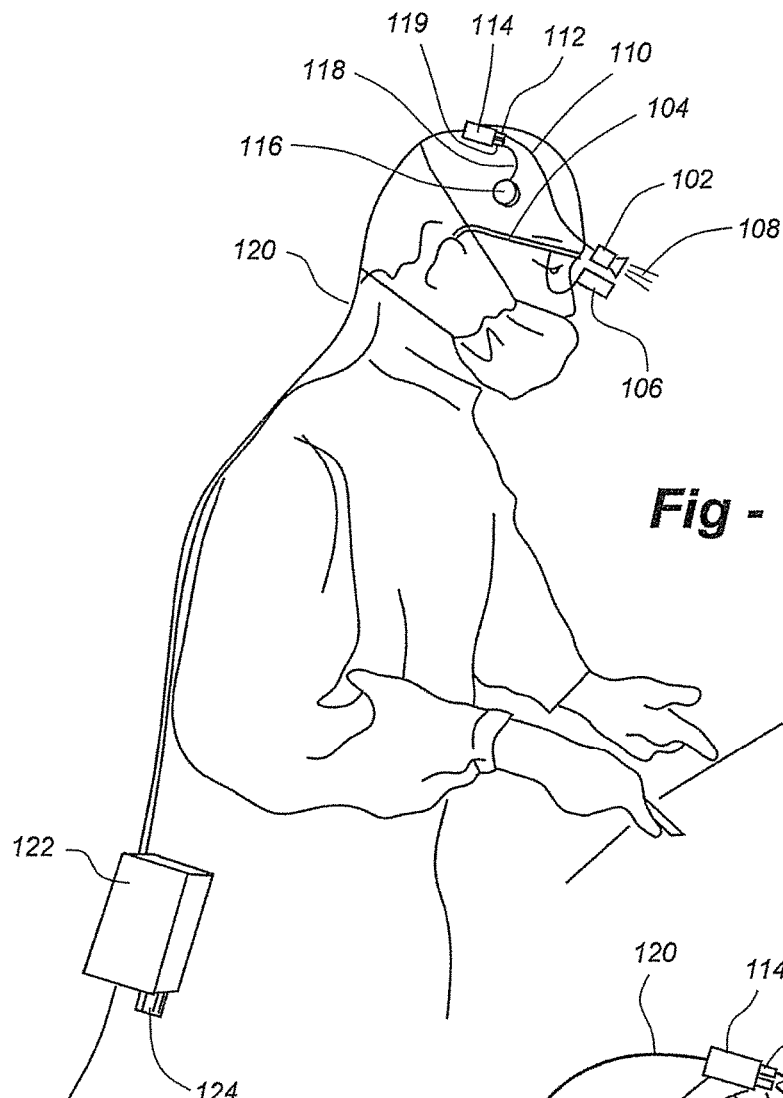
FIG. 1 is a drawing of an embodiment of the invention using an eyeglass frame mounted headlight.

FIG. 1 is a drawing of an embodiment of the invention using an LED headlight 102 mounted to eyeglass frames 104. In all embodiments, the light source may be permanently connected or temporarily coupled by way of a clip-on structure. Loupes 106, either the flip-up type or through-the-lens (TTL) type may be provided in conjunction with light source 102.

The light source 102 includes beam-forming and/or focusing optics (not shown) to produce a desired beam pattern 108. The LED(s) are powered through cable 110 which is ultimately connected to remote power supply and controller 122, which may be belt-worn, through combination cable 120. The system also includes an infrared (IR) sensor module 116 that is also coupled to the power supply and controller 122 through combination cable 120.

While the light 102 and IR sensor may be connected to the unit 122 directly, in the preferred embodiment, cable 110 from the light connects to a coupling unit 114 through electrical connector 112, and cable 118 from the sensor connects to the coupling unit 114 through electrical connector 119, enabling either or both of the cables 110, 118 to be disconnected. The power supply and control unit 122 contains rechargeable batteries that are replenished via connect to a changer shown in the block diagram of FIG. 3. A manual control knob 124 may be provided to establish a desired level of brightness prior to ON/OFF control using the IR sensor.

IR sensor 116 is preferably a miniature passive IR sensor available from various suppliers. For example, the KC7783 PIR Sensor Module is a pyroelectric sensor module developed for human body part detection. A PIR detector, combined with a Fresnel lens, are mounted on a compact printed circuit board together with an analog IC (the KC778B) providing a TTL output that can be directly connected to a microcontroller or logic device disposed in remote unit 122. Again, this PIR sensor is one of many applicable to the invention.

Figure 2:
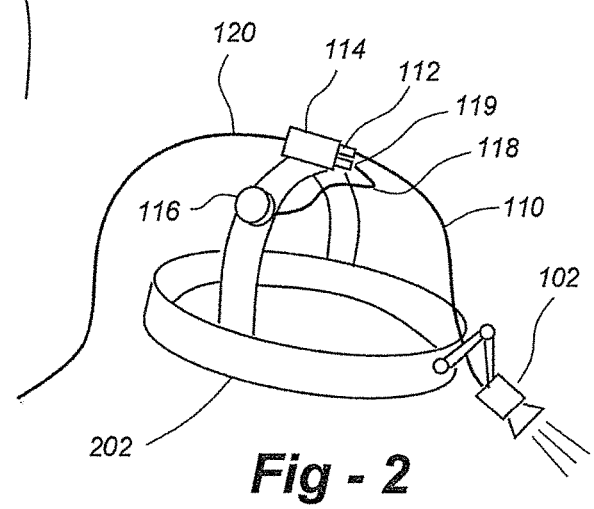
FIG. 2 is a drawing of an embodiment of the invention using headband-mounted headlight.

The IR sensor may be mounted at any convenient location, though in the preferred embodiment, it is head-mounted, whether clipped to a head mask or other clothing, mounted on eyeglass frames, the light source itself, or a headband 202 of the type depicted in FIG. 2. The sensor is preferably oriented in a direction that is least likely to experience false activation from bright/warm lights, other individuals, and so forth.

In operation, a user waves their hand in the proximity of the sensor 116, which causes the light 102 to turn ON and OFF without physical contact. In the preferred embodiment, the detection distance of the sensor is adjusted to be on the order of about 5 to 10 cm to enhance proper operation. This activation distance, as well as the field of view, may be adjusted through electrical component selection and/or sensor lens optics, materials, translucency, and so forth.

Figure 3:
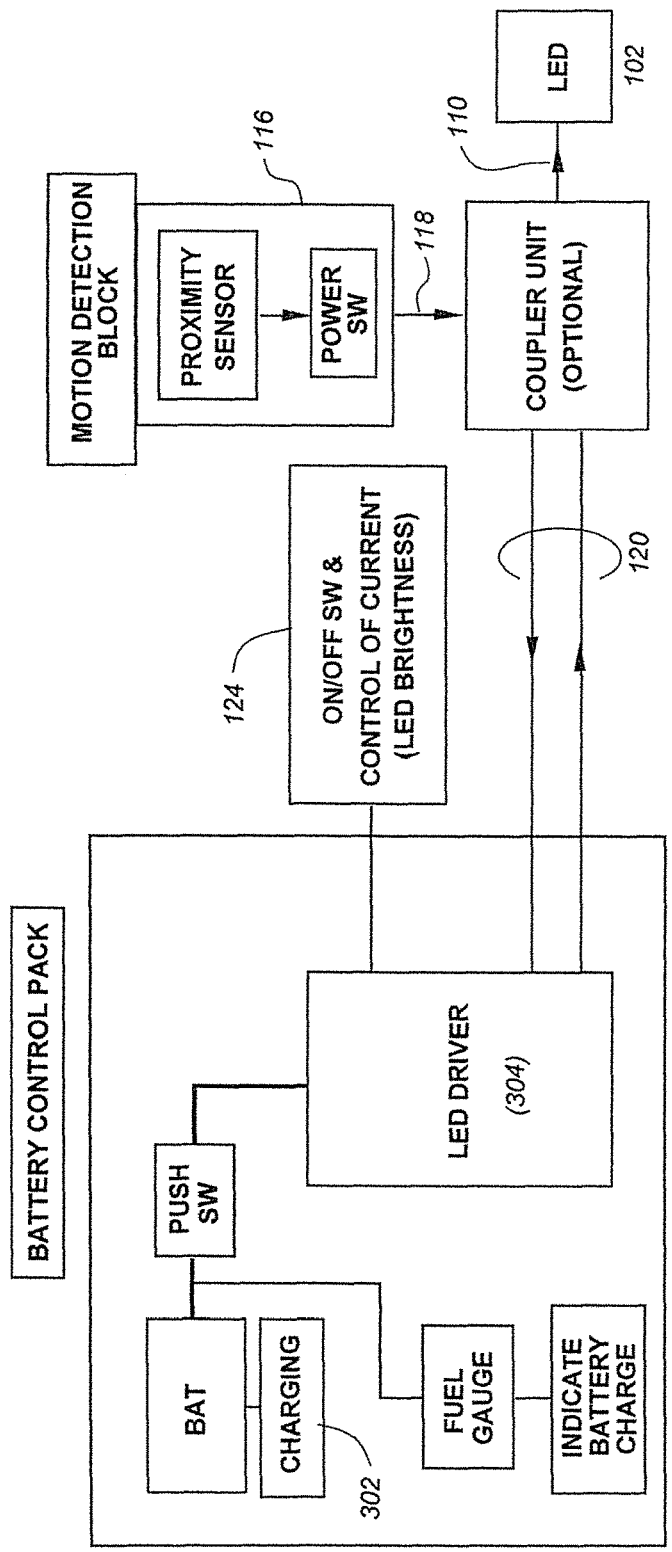
FIG. 3 is a block diagram of the invention showing cables, light emitter, and sensor.

Referring to FIG. 3, the electrical circuitry 304 in the power supply and control unit 122 may be designed to simply toggle the light ON/OFF with each hand/body part detection. In other words, if the light is ON, the user waves their hand to turn it OFF and vice-versa. Further, if the light is ON or OFF by mistake, one wave of the hand resents the light to the correct activation.

Figure 4:
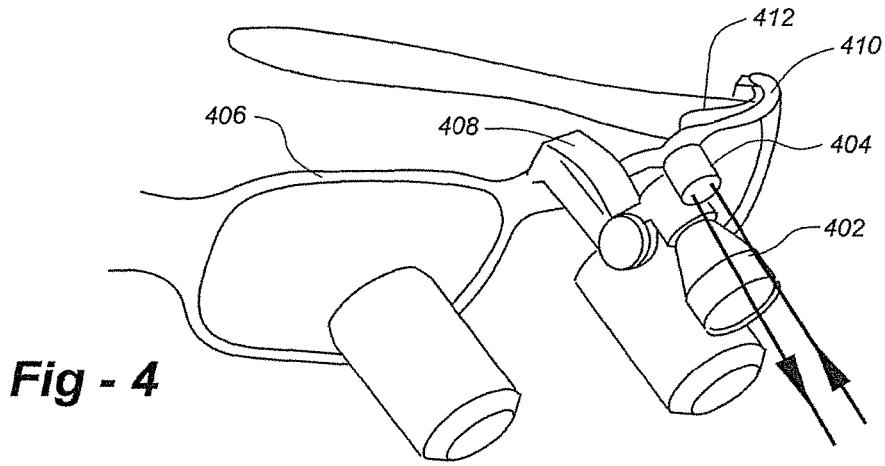
FIG. 4 is a drawing that illustrates an embodiment of the invention using an active IR sensor with a variable threshold to customize the activation distance.

FIG. 4 is a drawing that illustrates an embodiment of the invention using an active optical proximity sensor with a variable threshold to customize the activation distance. The sensor is mounted in a housing 404 which includes a light emitter and detector described in further detail below. The housing 402 is an LED light source which is coupled to eyeglass frames 406 through mechanically adjustable coupler 408. The frames 406 are shown with through-the-lens loupes though the invention is not limited by the choice of loupes, coupler or particular light unit. The optical orientation of the optical proximity sensor is preferably aligned with the optical axis of light 402 though this is also not necessary as a user may desire sidewise control. Cable 410 is routed to a power source and control unit for the headlamp 404, whereas cable 412 is routed to a separate power source and control unit for the proximity detector 404.

Figure 5:
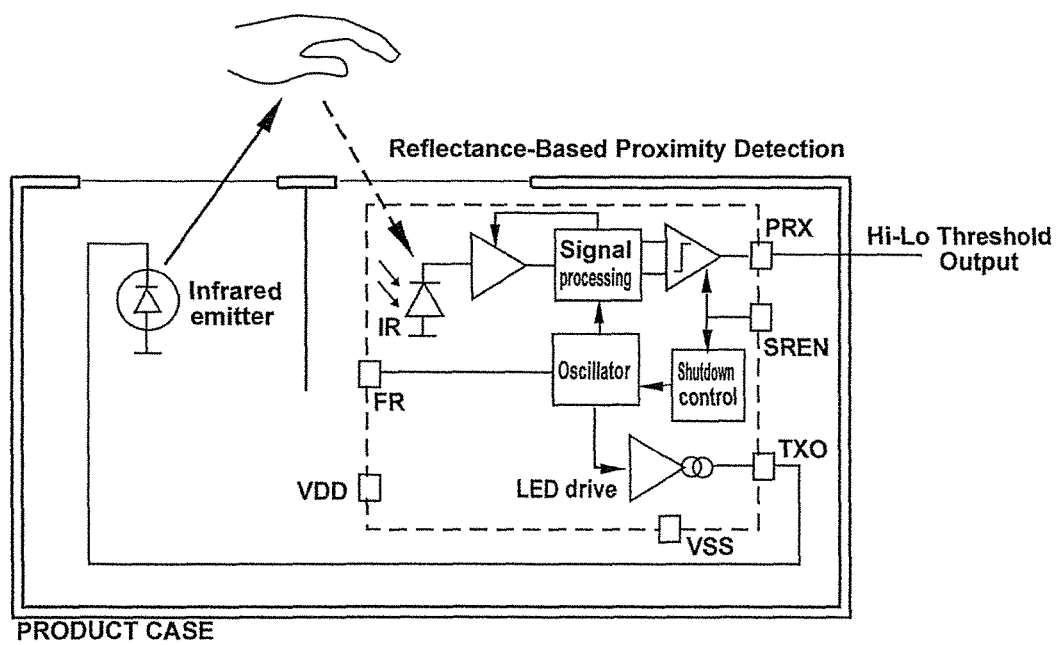
FIG. 5 is a block diagram of an optical proximity detector applicable to the invention.
Figure 6:
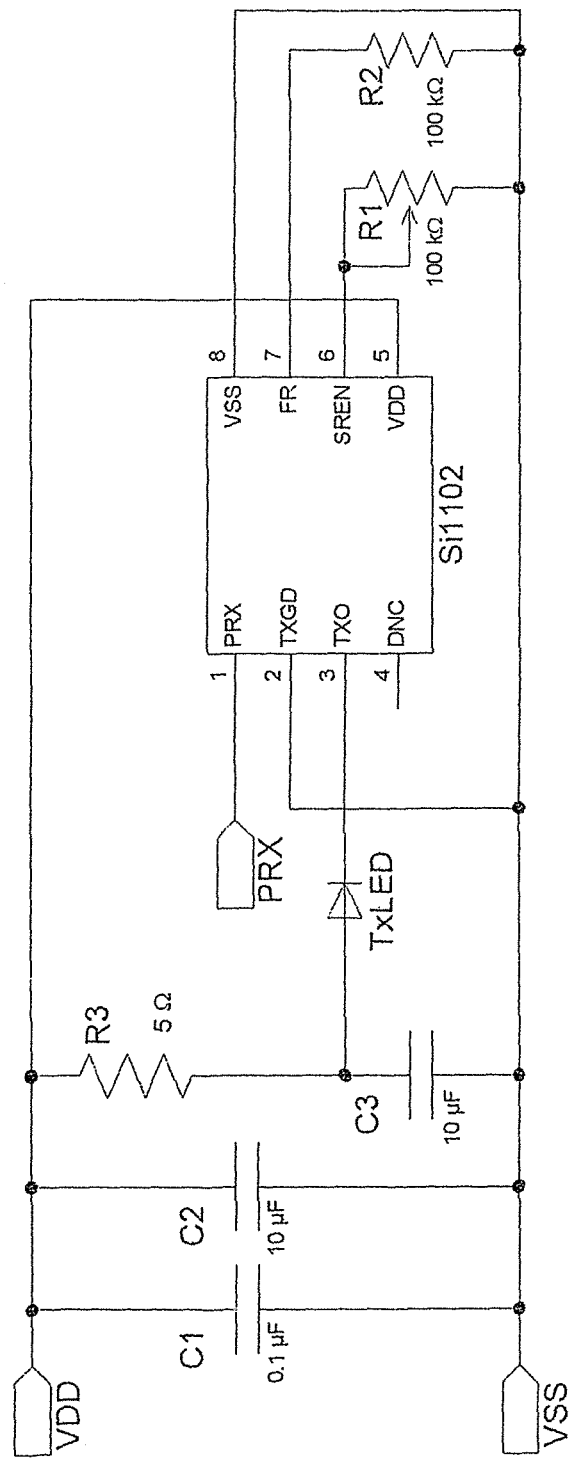
FIG. 6 is a schematic depicting how the detector of FIG. 5 may be implemented.

FIG. 5 is a block diagram of the optical proximity detector, which in this case happens to be a Si1102 device made by Silicon Labs. Comparable units from other manufacturers may be substituted. FIG. 6 is a schematic depicting how the detector of FIG. 5 may be implemented. The Si1102 is an active optical reflectance proximity detector with a simple on/off digital output whose state is based upon the comparison of reflected light against a set threshold. An LED sends light pulses whose reflections reach a photodiode and are processed by the Si1102's analog circuitry. If the reflected light is above the detection threshold, the Si1102 asserts the active-low PRX output to indicate proximity. The potentiometer, R1, is used to set the proximity detection threshold. The Si1102 periodically detects proximity at a rate that can be programmed by a single resistor (R2). Although the thresholds are normally set using a potentiometer for R1 (or R2), it is possible to digitally control various resistance values by using MCU GPIO pins to switch-in different value resistors (or parallel combinations of resistors). Regardless of which resistor(s) are used to control activation proximity, they may be located on unit 404 or remotely in the power supply/control unit for the sensor unit. In the preferred embodiment, a user is able to adjust the ON/OFF proximity of a hand, for example, to be in the range of one to 12 inches or more.

Figure 7:
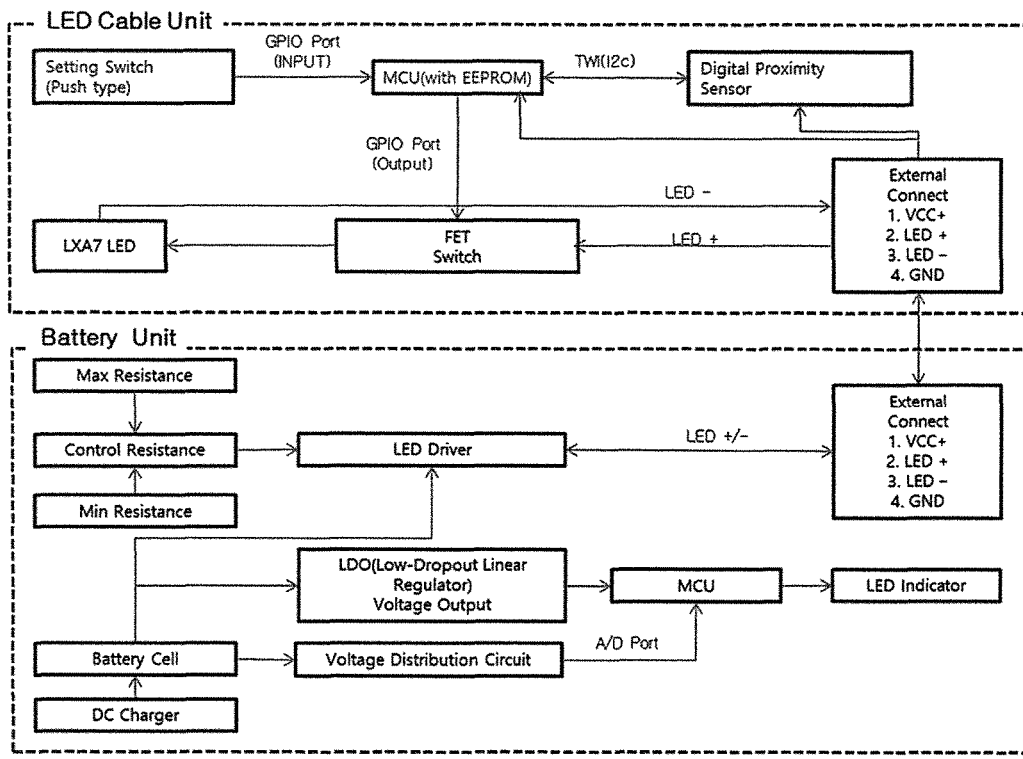
FIG. 7 is a block diagram of a microprocessor-based (MCU) version of a motion-activated LED headlamp controller with proximity adjustment.

FIG. 7 is a block diagram of a microprocessor-based (MCU) version of a motion-activated LED headlamp controller with proximity adjustment. All of the electronics associated with proximity control of the LED is disposed in the LED Cable Unit, such that only power at fixed voltages needs be delivered to the LED Cable Unit through a single cable from the Battery Unit. In particular, an External Connect in the Battery Unit delivers LED +/− at a fixed voltage as well as VCC+ and ground to power the MCU and other components in the LED Cable Unit, also at a fixed voltage. As with other embodiments disclosed herein, by placing all proximity ON/OFF and threshold controls at the location of the LED light source, no feedback or control signals need to be routed from the LED Cable Unit back to the Battery Unit. Thus, in the configuration of FIG. 4, only a single power cable needs to be routed from the Battery Unit to the sensor 404 and LED source 402.

In the block diagram of FIG. 7, an EEPROM associated with the MCU stores the threshold value enabling the Proximity Sensor (PS) to turn the FET Switch (and LED light) ON and OFF. If the signal from the PS becomes stronger than the stored threshold value, the MCU is operative to turn the FET and LED ON and OFF. If a user desires a different activation distance, they can replace the existing threshold value using the pushbutton Setting Switch. When this reset button is pushed, the MCU detects the signal reflected from an object (such as hand) at a desired activation distance and stores this new criteria value in the EEPROM of the MCU. The resetting function will allow users to decide their desirable activation distance.

Figure 8:
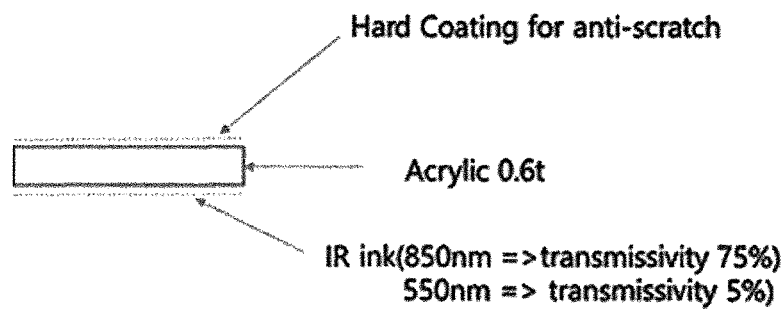
FIG. 8 is a cross section of an absorption-type IR filter applicable to the invention.

The LED light source includes an internal IR LED (about 900 nm), with IR filters being used to block stray IR signals from outside light sources such as room lights and dental or surgical overhead lights. Applicable IR filters have a high transmissivity for the internal IR wavelength and the low transmissivity for other wavelengths. Without the use of such filters the signal detection distance may vary significantly. FIG. 8 is a cross section of an absorption-type IR filter applicable to the invention, with the understanding that other types of filters may be used so long as they have a high transmissivity for the internal IR wavelength and the low transmissivity for other wavelengths.

The invention claimed is:

1. A motion-activated headlamp with adjustable proximity control, comprising:
   a battery unit;
   a head-mounted unit, including:
      a light source:
      a proximity sensor;
      a power switch receiving power from the battery unit;
      a user control;
      a memory; and
      a controller operative to perform the following functions:
         (a) store a threshold signal in the memory when a hand or other object is detected at a control distance from the proximity sensor when the user control is activated during a proximity programming mode, and
         (b) control the power switch, causing the light source to ON and OFF, if a hand or other object is detected at the control distance in accordance with the stored threshold value.

2. The motion-activated headlamp of claim 1, wherein the light source is a light-emitting diode (LED).

3. The motion-activated headlamp of claim 1, wherein the proximity sensor is an active infrared (IR) sensor including an IR emitter and an IR detector.

4. The motion-activated headlamp of claim 1, wherein the battery unit provides fixed-voltage power signals to the head-mounted unit such that no control signals are required from the head-mounted unit to the battery unit.

5. The motion-activated headlamp of claim 1, wherein the power switch receives a fixed-voltage power signal directly from the battery unit.

6. The motion-activated headlamp of claim 1, including a mechanism to attach the head-mounted unit to eyeglass frames or to a headband.

7. The motion-activated headlamp of claim 1, wherein the control distance is adjustable in the range of 1 to 12 inches or more.

8. The motion-activated headlamp of claim 1, wherein the memory is a non-volatile memory.

9. The motion-activated headlamp of claim 1, wherein the power switch is a FET switch.

10. The motion-activated headlamp of claim 1, wherein the head-mounted unit includes a single housing.

11. The motion-activated headlamp of claim 1, wherein the head-mounted unit includes a separate housing for the light source.

12. The motion-activated headlamp of claim 1, wherein the proximity sensor further includes a bandpass filter based on a predetermined IR wavelength.

13. The motion-activated headlamp of claim 1, wherein the proximity sensor further includes a bandpass filter based on a predetermined IR wavelength centered around 900 nm.

* * * * *